(12) United States Patent
Motta et al.

(10) Patent No.: US 12,357,282 B2
(45) Date of Patent: Jul. 15, 2025

(54) INTERSTITIAL FLUID REMOVAL DEVICE

(71) Applicant: IMCOMET B.V., Rotterdam (NL)

(72) Inventors: Alexandre Charles Roger Motta, Rotterdam (NL); Varsha Sakina Thakoersing, Rotterdam (NL); Richardus Paulus Anton Oranje, Rotterdam (NL)

(73) Assignee: IMCOMET B.V., Rotterdam (NL)

( * ) Notice: Subject to any disclaimer, the term of this patent is extended or adjusted under 35 U.S.C. 154(b) by 635 days.

(21) Appl. No.: 17/776,386

(22) PCT Filed: Nov. 19, 2020

(86) PCT No.: PCT/NL2020/050723
§ 371 (c)(1),
(2) Date: May 12, 2022

(87) PCT Pub. No.: WO2021/101375
PCT Pub. Date: May 27, 2021

(65) Prior Publication Data
US 2022/0395258 A1    Dec. 15, 2022

(30) Foreign Application Priority Data
Nov. 21, 2019 (NL) ...................................... 2024277

(51) Int. Cl.
*A61B 5/00*        (2006.01)
*A61B 10/00*       (2006.01)
*A61M 5/32*        (2006.01)

(52) U.S. Cl.
CPC ....... *A61B 10/0045* (2013.01); *A61M 5/3295* (2013.01); *A61B 2010/008* (2013.01)

(58) Field of Classification Search
CPC .......... A61B 10/0045; A61B 2010/008; A61B 5/150396; A61B 5/150984;
(Continued)

(56) References Cited

U.S. PATENT DOCUMENTS 6,132,755 A * 10/2000 Eicher ............... A61M 37/0015
424/427
6,398,931 B1 * 6/2002 Burchette .......... G01N 27/4035
204/417
(Continued)

FOREIGN PATENT DOCUMENTS

WO    2005/000382 A2    1/2005
WO    2010/122222 A2    10/2010
(Continued)

OTHER PUBLICATIONS

International Search Report (ISR) for PCT/NL2020/050723 mailed Feb. 2, 2021 (5 pages).
(Continued)

*Primary Examiner* — May A Abouelela
(74) *Attorney, Agent, or Firm* — NIXON PEABODY LLP (57) ABSTRACT

An interstitial fluid removal device including a first needle, a second needle, a fluid injector and an interstitial fluid extractor. The first needle is configured for insertion in a tissue of a multicellular organism to provide a fluid inlet channel. The second needle is configured for insertion in a tissue of a multicellular organism to provide an interstitial fluid outlet channel. The fluid injector is arranged in fluid communication with both a fluid source and the first needle and configured to inject a fluid in the tissue of the multicellular organism. The fluid extractor is arranged in fluid communication with the second needle and configured to extract interstitial fluid from the tissue of the multicellular organism. The fluid injector and the fluid extractor are independently and/or simultaneously operable with respect to each other.

20 Claims, 7 Drawing Sheets

(58) Field of Classification Search
CPC ....... A61B 5/150022; A61B 5/150053; A61M 5/3295; A61M 5/3298
See application file for complete search history.

(56) References Cited

U.S. PATENT DOCUMENTS

| | | | | |
|---|---|---|---|---|
| 6,652,720 | B1* | 11/2003 | Mansouri | G01N 27/3271 204/415 |
| 7,344,499 | B1* | 3/2008 | Prausnitz | A61B 5/150022 600/347 |
| 9,987,427 | B1 | 6/2018 | Polsky et al. | |
| 10,638,963 | B2* | 5/2020 | Beyerlein | A61B 5/150442 |
| 11,060,989 | B2* | 7/2021 | Hanson | G01N 27/026 |
| 11,766,203 | B2* | 9/2023 | Miller | A61B 5/150984 600/309 |
| 2002/0188185 | A1* | 12/2002 | Sohrab | A61B 5/14514 600/347 |
| 2004/0034318 | A1* | 2/2004 | Fritz | A61B 5/150519 604/19 |
| 2004/0127929 | A1* | 7/2004 | Roe | A61B 5/150503 606/181 |
| 2004/0176732 | A1* | 9/2004 | Frazier | A61M 37/0015 977/932 |
| 2005/0113739 | A1* | 5/2005 | Stiene | A61B 5/15087 600/583 |
| 2005/0177071 | A1* | 8/2005 | Nakayama | A61B 5/150129 600/583 |
| 2007/0158212 | A1* | 7/2007 | Filanovsky | G01N 27/4045 205/780.5 |
| 2007/0191696 | A1* | 8/2007 | Mischler | G01N 21/552 600/347 |
| 2007/0270672 | A1* | 11/2007 | Hayter | A61B 5/150526 600/309 |
| 2008/0221408 | A1* | 9/2008 | Hoarau | A61B 5/0059 604/503 |
| 2008/0234562 | A1* | 9/2008 | Jina | A61B 5/150358 600/365 |
| 2009/0036795 | A1* | 2/2009 | Duineveld | A61B 5/150099 600/573 |
| 2010/0056989 | A1* | 3/2010 | McKay | A61B 17/3478 604/38 |
| 2010/0256524 | A1* | 10/2010 | Levinson | A61B 5/151 600/576 |
| 2011/0105942 | A1* | 5/2011 | Lim | A61B 5/0531 600/547 |
| 2011/0172559 | A1* | 7/2011 | Fei | A61B 5/150213 600/583 |
| 2011/0224515 | A1* | 9/2011 | Mir | A61B 5/15151 600/317 |
| 2011/0264048 | A1* | 10/2011 | O'Dea | A61M 37/0015 604/173 |
| 2012/0277697 | A1* | 11/2012 | Haghgooie | A61B 5/14514 604/327 |
| 2013/0158468 | A1* | 6/2013 | Bernstein | A61B 5/150969 604/173 |
| 2013/0211289 | A1* | 8/2013 | Moga | A61B 5/157 600/583 |
| 2013/0253289 | A1* | 9/2013 | Hadvary | A61B 5/150664 600/309 |
| 2013/0263997 | A1* | 10/2013 | Down | A61M 37/0015 156/60 |
| 2013/0306155 | A1* | 11/2013 | Mathus | B01L 3/0217 137/1 |
| 2013/0317391 | A1* | 11/2013 | Bullington | A61B 5/15003 600/578 |
| 2014/0114279 | A1* | 4/2014 | Klinghoffer | A61K 49/0008 604/173 |
| 2014/0148669 | A1* | 5/2014 | Garcia Saban | A61B 5/150412 600/347 |
| 2015/0201877 | A1* | 7/2015 | Gasparyan | A61B 5/150488 604/272 |
| 2015/0202418 | A1* | 7/2015 | Simon | A61M 37/0015 604/319 |
| 2015/0208984 | A1* | 7/2015 | Huang | A61B 5/685 600/393 |
| 2016/0029937 | A1* | 2/2016 | Sia | A61B 5/1459 600/479 |
| 2016/0051981 | A1* | 2/2016 | Berthier | A61B 5/1411 600/573 |
| 2016/0166185 | A1* | 6/2016 | Liepmann | A61B 5/150503 600/365 |
| 2016/0296149 | A1* | 10/2016 | Polsky | A61B 5/14546 |
| 2017/0023546 | A1* | 1/2017 | Holmes | A61B 5/150343 |
| 2017/0080164 | A1* | 3/2017 | Kwon | A61M 5/3298 |
| 2017/0122846 | A1* | 5/2017 | Holmes | G01N 33/491 |
| 2017/0164933 | A1* | 6/2017 | Coats | A61B 10/0045 |
| 2017/0172481 | A1* | 6/2017 | Berthier | A61B 5/150984 |
| 2017/0304553 | A1* | 10/2017 | Bender | A61M 5/31 |
| 2018/0070869 | A1* | 3/2018 | Ionescu | A61B 5/150358 |
| 2018/0161563 | A1* | 6/2018 | Renlund | A61B 5/14532 |
| 2018/0256086 | A1* | 9/2018 | Polsky | A61B 5/150068 |
| 2018/0264043 | A1* | 9/2018 | Pettine | A61K 35/28 |
| 2018/0338713 | A1* | 11/2018 | Polsky | A61B 5/157 |
| 2020/0230388 | A1* | 7/2020 | Daniele | A61M 37/0015 |
| 2022/0240815 | A1* | 8/2022 | Chae | A61B 5/150022 |
| 2022/0322981 | A1* | 10/2022 | Chae | A61B 5/15016 |

FOREIGN PATENT DOCUMENTS

| | | |
|---|---|---|
| WO | 2014/093934 A1 | 6/2014 |
| WO | 2016/164208 A1 | 10/2016 |

OTHER PUBLICATIONS

Written Opinion for PCT/NL2020/050723 mailed Feb. 2, 2021 (7 pages).

* cited by examiner

INTERSTITIAL FLUID REMOVAL DEVICE

BACKGROUND

The present invention relates to an interstitial fluid removal device and system, a method for manufacturing an interstitial fluid removal system, and a method for treating a subject having a skin tumor.

WO 2016/164208 A1 describes a transdermal and/or intradermal diagnostic device comprising a hollow microneedle interstitial fluid extraction device. In one embodiment, the microdialysis-inspired device initially contains a saline solution. This solution is injected into the skin through a hollow microneedle array to mix with the interstitial fluid in said skin. After said mixing the fluid is retrieved again, together with mixed biomarkers, back through the same hollow microneedle array via negative pressure from a pump. About 1-10 µl of interstitial fluid may be collected per needle in the microneedle array. The maximum volume of interstitial fluid that can be collected with the device of WO 2016/164208 A1 is 50 µl.

U.S. Pat. No. 9,987,427 B1 describes a device for detecting and/or monitoring one or more markers in a sample. In particular, the device integrates a plurality of hollow needles configured to extract a fluid sample from a subject, as well as transducers to detect a marker of interest. In U.S. Pat. No. 9,987,427 B1 a "sense-respond" platform is disclosed which first extracts some fluid from a subject through a first needle. Then, this fluid is tested. Depending on the outcome of the test, drugs can be injected in the subject through a second needle. If the reservoir containing the fluid is full, it can be emptied by re-injecting the extracted fluid into the subject through a return needle.

WO 2005/000382 A2 relates to rotating microneedles and microneedle array that "drill" holes into a biological barrier, such as skin. The holes can be of controlled depth and diameter and suitable for microsurgery, administering drugs and withdrawal of body fluids. In a first example of WO 2005/00382 A2 ("Example 2"), interstitial fluid is collected with a microneedle device. In a second example of WO 2005/000382 A2 ("Example 3"), fluid is microinjected using the microneedle device.

WO 2010/122222 A2 discloses a microfluidic needle for the collection of a blood sample or for the manipulation of single cells. The microfluidic needle comprising at least two microfluidic channels. The needle can be used for injection and/or sampling fluids to/from tissue or individual cells.

SUMMARY OF THE INVENTION

However, for certain applications it may be desirable to collect a significantly higher volume of interstitial fluid than is possible with the known devices. It is therefore an object of the present invention to provide an interstitial fluid removal device with which relatively large amounts of interstitial fluid can be collected.

Therefore, according to a first aspect of the invention an interstitial fluid removal device comprising a first needle, a second needle, a fluid injector and an interstitial fluid extractor is provided, wherein
the first needle is configured for insertion in a tissue of a multicellular organism to provide a fluid inlet channel;
the second needle is configured for insertion in a tissue of a multicellular organism to provide an interstitial fluid outlet channel;
the fluid injector is arranged in fluid communication with both a fluid source and the first needle and configured to inject a fluid in the tissue of the multicellular organism;
the fluid extractor is arranged in fluid communication with the second needle and configured to extract interstitial fluid from the tissue of the multicellular organism, and
wherein the fluid injector and the fluid extractor are independently and/or simultaneously operable with respect to each other,
wherein a distance between a needle tip of the first needle and a needle tip of the second needle is smaller than 3 mm, and
wherein opening of the first needle tip and the opening of the second needle tip face towards each other.

Interstitial fluid, as used herein, refers to the extracellular fluid that fills the spaces between most of the cells of a multicellular organism, e.g. a body (e.g. animal, mammal, human), an organoid or a tissue grown in vitro, and provides a substantial portion of the liquid environment of the multicellular organism. For instance, the interstitial fluid may comprise molecules or proteins such as chemokines, cytokines, enzymes, soluble extracellular matrix proteins, exosomes, extracellular vesicles and apoptotic bodies, lipid mediators and others.

Organism, as used herein, refers to e.g. living organisms such as multicellular viruses, bacteria, animals, mammals, humans, as well as organoids grown in vitro.

In one possible use of the interstitial fluid removal device, the interstitial fluid removal device is used for the removal of interstitial fluid from a body of a human, the tissue e.g. being skin tissue, possibly infected with a tumor.

When a tumor is present in the body, e.g. in the skin, the interstitial fluid contains altered levels of soluble signalling molecules and vesicles (also called: soluble factors). These soluble factors (disadvantageously) help to promote tumor growth, impair the function of the local immune cells and/or prevent the infiltration in the tumor, as well as induce metastasis (the spreading of the tumor to other parts of the body).

In other uses, the device may be used for the removal of interstitial fluid from a body of an animal, the tissue e.g. being skin tissue, possibly being affected with a tumor.

However also other applications of the presented interstitial fluid removal device are foreseen, such as treatment of atopic dermatitis, the treatment of psoriasis, and tissue engineering for the reconstruction of a skin.

The first needle of the interstitial fluid removal device is configured for insertion in a tissue of a multicellular organism, in vivo, ex vivo or in vitro, and defines a fluid inlet channel when inserted in said tissue. In use of the interstitial fluid removal device, the first needle is used to insert a fluid in the tissue of the multicellular organism. It is noted that the first needle may only be configured to insert or inject a fluid in the tissue of the multicellular organism, i.e. in embodiments the first needle is not configured to extract (interstitial) fluid from the tissue of the multicellular organism.

The first needle is arranged in fluid communication with the fluid injector and the fluid source. This allows the injection of a fluid stored in the fluid source in the tissue of a multicellular organism via the first needle.

The second needle of the interstitial fluid removal device is configured for insertion in the tissue of a multicellular organism, in vivo, ex vivo or in vitro and defines an interstitial fluid outlet channel when inserted in said tissue. In use of the interstitial fluid removal device, the second needle is used to extract interstitial fluid from the tissue of the multicellular organism. It is noted that the second needle may only be configured to extract or remove interstitial fluid from the tissue of the multicellular organism, i.e. in embodiments the second needle is not configured to inject or insert fluid into the tissue of the multicellular organism.

The second needle is arranged in fluid communication with the fluid extractor. This allows the extraction or removal of interstitial fluid from the tissue of the multicellular organism through the fluid outlet channel. For example the fluid extractor may be a suction pump or may use capillary forces to extract the interstitial fluid from the tissue.

Advantageously the fluid injector and the fluid extractor are independently and/or simultaneously operable with respect to each other. This allows fluid to be injected or inserted into the tissue of the multicellular organism independently and/or simultaneously with respect to the extraction or removal of interstitial fluid from said tissue.

The applicant has found that it is very difficult or even impossible to extract relatively large volumes of interstitial fluid from a tissue of a multicellular organism. The applicant has further found that it is very difficult to maintain a moderate or high flow rate of extracted interstitial fluid when extracting interstitial fluid for an elongated period of time, as the tissue "collapses" after extracting ISF for a moderate amount of time and extraction of interstitial fluid is no longer possible. After an initially successful extraction of a moderate amount of interstitial fluid, e.g. up to 10 µl per needle, the interstitial fluid is locally drained, the tissue collapses, and the outflow rate of interstitial fluid significantly drops or even stops. This makes it impossible to collect more interstitial fluid from that spot in the tissue. The interstitial fluid removal device according to the invention solves this problem by injecting a fluid in the tissue while interstitial fluid is removed or after interstitial fluid is removed, thereby allowing the formation of "new" interstitial fluid. As interstitial fluid is removed (drained) from the tissue, the empty space left by the removed interstitial fluid is filled with the newly injected carrier fluid. Soluble components (soluble signalling molecules and vesicles), also called soluble factors, present in the interstitial fluid surrounding the injected carrier fluid mix with the injected carrier fluid, such that the injected carrier fluid contains said soluble components and becomes interstitial fluid. This then allows the extraction of more soluble components from the tissue of the multicellular organism than when fluid is only extracted and no fluid is injected after or during extraction.

In embodiments, the fluid injector and the interstitial fluid extractor are operated simultaneously and continuously. For example the fluid injector and the interstitial fluid extractor may be operated continuously for a few minutes, e.g. 2 minutes or longer, such as 10 minutes or longer, to e.g. remove soluble components and/or biomarkers contained in the interstitial fluid from the tissue of the multicellular organism. Without wishing to be bound to a particular theory, it is expected by the applicant that, as the microenvironment surrounding the location of the fluid inlet channel and the fluid outlet channel is drained from soluble components and/or biomarkers, soluble components and/or biomarkers from the macro-environment surrounding said microenvironment will be attracted towards said microenvironment such that an equilibrium of the rate of soluble components and/or biomarkers in the (interstitial) fluid is maintained.

It may alternatively be advantageous to intermittently operate the fluid injector and the interstitial fluid extractor, e.g. by operating them both for a few minutes, such as for about 2 minutes or about 5 minutes or about 10 minutes, then stop operation for a short period of e.g. about 30 seconds or about 2 minutes or about 5 minutes or about 10 minutes or about 15 minutes, and then operate them again. This stop of operation allows the rate of soluble factors and/or biomarkers in the microenvironment surrounding the fluid inlet channel and the fluid outlet channel to increase in between operations by the migration of soluble factors and/or biomarkers from the macro-environment surrounding the micro-environment towards the micro-environment.

Further advantageously, by using a single needle to inject a carrier fluid, only the microenvironment surrounding the inlet channel is affected by said carrier fluid. Without wishing to be bound to a particular theory, it is expected by the applicant that the interstitial fluid initially present in the microenvironment surrounding the fluid inlet channel is pushed away when (a significant amount of) fluid is injected. When e.g. a tumor is present in the tissue, this may allow "harmful" soluble components in the interstitial fluid to spread and affect "healthy" tissue surrounding it. When only a limited amount of fluid is injected, through a single needle, this effect is minimized. It is furthermore preferred in this respect that the openings of the needles face towards each other. Preferably, to further reduce said spreading effect, the interstitial fluid extractor may in use be operated for a short amount of time, e.g. a few seconds, to remove some interstitial fluid, before the fluid injector is operated to inject the carrier fluid.

As the fluid injector and the interstitial fluid extractor can be operated simultaneously and/or independently, it is now possible with the ISF removal device according to the invention to extract or remove interstitial fluid from a tissue of a multicellular organism for continued periods of time, and thus to obtain larger quantities of said interstitial fluid/to drain more soluble factors from the tissue. Accordingly, the object of the invention is achieved.

Further advantageously, the interstitial fluid removal device may in certain applications be relatively comfortable to use and, when used on e.g. humans or animals, causes little or no pain, irritation or tension to said humans or animals. Further advantageously, the interstitial fluid removal device is minimally invasive, easy to apply and remove, stays in place for the desired duration of the treatment, and may not require preparation of the tissue before use, or only relatively minor preparation, e.g. the removal of hair from the tissue.

Turning back to the example of the treatment of skin cancer (i.e. cancer that originates from the skin's cells) it may be advantageous to remove interstitial fluid containing harmful soluble components in the area of the skin affected by the skin tumor (from the skin tumor itself) and/or in the area of the skin surrounding the skin tumor.

Removing interstitial fluid from a so-called "cold" tumor may transform the cold tumor into a "hot" tumor and increase the efficiency of therapeutic agents.

Advantageously, the hundreds of different soluble factors present in the interstitial fluid of the skin tumor may all be removed simultaneously when the interstitial fluid removal device according to the present invention is used. Treatment with therapeutic agents, as known in the art, typically allows to target only one or a few of said soluble factors.

The interstitial fluid removed from the tissue may e.g. consecutively be used for diagnostic purposes, e.g. biomarker analysis wherein the presence of certain biomarkers in the interstitial fluid is analysed. For example, it may be desirable to check whether a certain biomarker is present in the interstitial fluid. For example, a suitable treatment for a disease may be determined based on biomarkers in the interstitial fluid.

The interstitial fluid removed from the tissue may alternatively or additionally be used for health monitoring, e.g. to check the level of a certain biomarker over an elongated period of time (e.g. weeks, months, a year, longer). For example, the glucose level in the interstitial fluid may be measured with the interstitial fluid removal device as described herein.

In a further example, interstitial fluid may be extracted from reconstructed tissue to monitor the success rate of the reconstruction and perform further research.

In an embodiment, a penetration depth of the first needle is larger than a penetration depth of the second needle when the device is operated, e.g. because the first needle is longer than the second needle or because one of the needles is partially extracted after initial insertion. Preliminary tests, wherein pigment is injected in a (dead) test skin and wherein the interstitial fluid removal device is consecutively operated, surprisingly indicate that the removal rate of the pigment in the interstitial fluid is higher when the first needle has a larger penetration depth than when the penetration depths are the same. However, it is also possible that the penetration depths are the same or that the penetration depth of the second needle is larger than the penetration depth of the first needle.

In embodiments, the first needle and the second needle are separated from each other. That is, in embodiments the needles are not in direct fluidic contact with each other.

In an embodiment, the second needle is configured for insertion in the tissue of a multicellular organism in a direction substantially perpendicular with respect to a surface defined by said tissue. Possibly, also the first needle may be inserted in the tissue of the multicellular organism in a direction substantially perpendicular with respect to the surface defined by said tissue, the first needle and the second needle then being arranged substantially parallel with respect to each other. This may e.g. be preferred when a multitude of needles, e.g. 10 or more, e.g. one or more "first" needles and one or more "second" needles, e.g. several needle pairs as described in more detail in the below, is arranged in the tissue of the multicellular organism, e.g. as part of the interstitial fluid removal system that will be described in the below.

In an embodiment the first needle is configured for insertion in the tissue of a multicellular organism at an angle between 20° and 70° with respect to the second needle. Preferably said angle is between 30° and 60°, such as about 45°. Preliminary tests, wherein pigment is injected in a (dead) test skin and wherein the interstitial fluid removal device is consecutively operated, surprisingly indicate that the removal rate of the pigment in the interstitial fluid is higher when the first needle is inserted in the test skin at an angle of about 45° compared to when the needles are arranged parallel to each other. In this particular case, the second needle was inserted in the skin substantially perpendicular with respect to the surface defined by the skin, and the first needle was inserted in the skin at said angle of about 45° with respect to the second needle, but other configurations are of course possible.

In an embodiment the second needle is configured to be at least partially extracted from said tissue after insertion therein and before the fluid extractor is operated. After insertion of the second needle in the tissue, the tissue is pierced and an outflow channel results. Even in a live tissue, this outflow channel remains present for a considerable amount of time (up to multiple hours, depending on the tissue) after the second needle is (partially) extracted from the tissue. Preliminary tests, wherein pigment is injected in a (dead) test skin and wherein the interstitial fluid removal device is consecutively operated, surprisingly indicate that the removal rate of the pigment in the interstitial fluid is higher when the second needle is fully extracted from the test skin compared to when the second needle remains inserted in the test skin.

In an embodiment a distance between a needle tip of the first needle and a needle tip of the second needle is smaller than 2 mm, e.g. smaller than 1 mm, preferably smaller than 0.5 mm, such as smaller than 0.1 mm, or about 0.02 mm or smaller. The distance between the needle tips affects the size of the microenvironment from which interstitial fluid (soluble factors) is removed. When the distance between the needle tips is relatively small only minute pressures are required to inject fluid in the tissue and to extract interstitial fluid from the tissue which is on the one hand advantageous for the energy consumption of the interstitial fluid removal device and on the other hand, particularly when the interstitial fluid removal device is used on a human or an animal, as this is pleasant for said human or animal undergoing the treatment.

For example a distance between a needle tip of the first needle and a needle tip of the second needle is larger than 0, and may e.g. be larger than 0.01 mm, preferably larger than 0.015 mm, such as larger than 0.02 mm.

When seen in a front view, the "distance" between a needle tip of the first needle and a needle tip of the second needle is defined as the distance between the right wall portion of the left needle and the left wall portion of the right needle.

In an embodiment the first needle and the second needle are configured for insertion in a skin a of an animal, such as a mammal, or a human, preferably in the dermis layer of said skin. For example, the first needle and the second needle may have a penetration depth ranging between about 0.05 and 1.5 mm, such as for instance between about 0.1 and 1.4 mm, between 0.2 and 1.3 mm, between about 0.3 and 1.2 mm, between about 0.4 and 1.1 mm, between about 0.5 and 1.0 mm, or between about 0.6 to 0.9 mm, or preferably between 0.3 and 0.7 mm. For example the needles may be microneedles.

In an embodiment the interstitial fluid removal device further comprises a housing for receiving a needle pair, said first needle and said second needle forming said needle pair. Advantageously, the housing may e.g. fixate the position and orientation of the second needle with respect to the position and orientation of the first needle (and/or vice versa). Advantageously, the housing may e.g. allow to insert the first and the second needle in the tissue of the multicellular organism simultaneously.

In an embodiment, the interstitial fluid removal device comprises several, i.e. two or more, "first" needles for providing a fluid inlet channel and for injecting a fluid and/or several, i.e. two or more "second" needles for providing a fluid outlet channel and for extracting interstitial fluid. For example one outlet channel may be surrounded by several inlet channels. For example, one inlet channel may be surrounded by several outlet channels. A diameter of the inlet channel (/first needle) may be different (larger or smaller) than a diameter of the outlet channel (/second needle).

In an embodiment the fluid is a fluid selected from the non-exhaustive and exemplary list comprising surface tension modifiers (e.g. polyethylene glycol derivatives), osmolality modifiers (e.g. sodium chloride, sucrose, or water), pH modifiers (e.g. bicarbonate buffers), chelating agents (e.g. EDTA) and bio-active molecules (e.g. proteins, drugs), possible mixed with another fluid. In embodiments, the fluid may be mixed with or contain a drug for delivery in the tissue of a multicellular organism, e.g. a skin of a mammal, through the first needle. In embodiments, the fluid may be heated or cooled with respect to a temperature of the multicellular organism.

In an embodiment the fluid injector has a flow rate of at least 6 µl/h, or at least 0.1 µl/min, per needle. For example, when the fluid injector is connected to two first needles (i.e. wherein the interstitial fluid removal device comprises two first needles configured for insertion in a tissue of a multicellular organism to provide a fluid inlet channel), the fluid injection may have a flow rate of at least at least 12 µl/h. In case there are two first needles, there may alternatively be two fluid injectors each having a flow rate of at least 6 µl/h. The flow rate of the fluid extractor may be equal to the flow rate of the fluid injector. A maximum flow rate of the fluid injector (and/or fluid extractor) may be up to 125 µl/min.

For example between about 50 µl to 1500 µl of interstitial fluid may be removed per day (24 hours) per needle.

A second aspect of the invention relates to an interstitial fluid removal system, comprising a patch member which includes at least two recesses and at least two interstitial fluid removal devices as described in the above, wherein a said interstitial fluid removal device is arranged in at least two of said recesses. Possibly, the patch member comprises more than two recesses, some or all of these recesses also being provided with an interstitial fluid removal device. Preferably the interstitial fluid removal system is tailored to the specific needs of a multicellular organism, e.g. with the method for manufacturing an interstitial fluid removal system as described below. This allows to remove interstitial fluid from several positions, and possibly also from different depths, of the tissue, simultaneously.

In an embodiment a penetration depth of the interstitial fluid removal device arranged in a first one of said recesses differs from a penetration depth of the interstitial fluid removal device arranged in a second one of said recesses. This may e.g. be achieved by having different recess depths, and/or by having needles of a different length. As described in the above, the present device and system may e.g. in a non-limiting embodiment be advantageous for the removal of interstitial fluid around or from a skin tumor. Depending on the layout of the tumor, it may be desired to remove interstitial fluid at different skin depths. More particularly, after taking into account the ultrastructure of the skin tissue (e.g. presence of blood vessels, collagen density and fibres orientation, and cell density), different penetration depths for different interstitial fluid removal devices may be determined.

In an embodiment, a distance between the first interstitial fluid removal device and the second interstitial fluid removal device of the interstitial fluid removal system is larger than the distance between the first needle and the second needle of the respective interstitial fluid removal devices. For example the distance between the first interstitial fluid removal device and the second interstitial removal device may be sufficiently large to separate the microenvironment affected by the first interstitial fluid removal device from the microenvironment affected by the second interstitial fluid removal device. In other embodiments, said microenvironments may touch and/or overlap.

A third aspect of the present invention relates to a method for manufacturing an interstitial fluid removal system as described in the above, comprising the steps of:
providing a 3D clinical representation of a skin tumor of a patient, the patient being human or non-human;
designing a patch member based on said clinical representation, the patch member having at least two recesses, at least two of the recesses preferably having a different depth;
placing a housing in at least two of the recesses, the housing comprising at least a first needle and a second needle, wherein at least the lengths of the first needle and the second needle are based on said clinical representation;
fluidly coupling the first needles of the housings to one or more fluid injectors;
fluidly coupling the second needles of the housings to one or more interstitial fluid extractors.

With this method the interstitial fluid removal system may be optimally tailored to a skin tumor of a patient, allowing to remove interstitial fluid from different depths in or around the tumor. Of course it is not required that the skin tumor is still present in the body of the patient. For example the skin tumor may also be at least partially extracted from the body of the patient and e.g. further grown in an in vitro environment.

Of course, the interstitial fluid removal system may also be manufactured based on a 3D representation of an organoid or tissue which is grown in vitro, or a part of an organoid or tissue, or the surroundings of an organoid or tissue (containing no cells or other cell types) which is grown in vitro.

For example, based on the 3D clinical representation, the size of the patch member may be chosen. For example, based on the 3D clinical representation, the length of the needles, the distance between the needles, the diameter of the needles and/or the depth of the recess may be chosen.

A fourth aspect of the present invention relates to a method for treating a subject with skin tumor, the subject being human or non-human, the method comprising the step of removing an amount of interstitial fluid from said skin tumor with the interstitial fluid removal device as described in the above, or with the interstitial fluid removal system as described in the above.

The applicant has found that by removing an amount of interstitial fluid from within the skin tumor, with or without the interstitial fluid from the surrounding of a skin tumor (e.g. melanoma and/or basal cell carcinoma and/or squamous cell carcinoma), by using the method as taught herein, several beneficial effects are observed including: 1) impairment of tumor growth, 2) impairment of the tumor's ability to undergo metastasis or spread to other parts of the body, and 3) improvement of host immunity (e.g. host's immune cells can better infiltrate the tumor, detect and eliminate (kill) cancer cells). Globally, the beneficial effects can result in reduced tumor volume and increased survival over time.

In addition, removal of an amount of interstitial fluid from within and/or from the surrounding of a skin tumor, in a subject undergoing a drug treatment (e.g. oral or systemic administration of a cancer therapeutic such as an immune checkpoint blockade inhibitor, a chemotherapeutic, etc.), may enhance the effect of the drug treatment (compared to drug treatment alone).

Without wishing to be bound to any theories, it is believed that the beneficial effects associated with the method as taught herein occur because the removal of an amount of interstitial fluid from within and/or from the surrounding of a tumor leads to:

1) a temporary void (relatively empty or emptier space), which is (at least partially) refilled with healthy interstitial fluid originating from neighbouring healthy cells. and/or 2) the skin cancer microenvironment is depleted from deleterious molecules, which either counteract the effect of cancer drugs and/or contribute to the tumor's ability to grow, escape immune surveillance and/or undergo metastasis so as to spread to other parts of the body. By depleting/draining such deleterious molecules, cancer drugs can exert their effects without interference, which leads to an increase in skin tumor cell death, and ultimately decreased skin tumor volume or disappearance of the skin tumor, and increased survival.

A fifth embodiment of the present invention relates to a method for the removal of interstitial fluid from the tissue of a multicellular organism, the method comprising the steps of:

inserting a first needle in a tissue of a multicellular organism;
connecting a fluid injector to the first needle;
inserting a second needle in a tissue of a multicellular organism;
connecting a fluid extractor to the second needle;
operating the fluid injector and the fluid extractor.

BRIEF DESCRIPTION OF THE FIGURES

These and other aspects of the present invention will be elucidated further with respect to the attached figures. In said figures, FIG. 1A schematically illustrates a first embodiment of an interstitial fluid removal device inserted in a tissue of a multicellular organism;

FIG. 10 schematically illustrates a third embodiment of an interstitial fluid removal device inserted in a tissue of a multicellular organism;

DETAILED DESCRIPTION

Figure 1A:
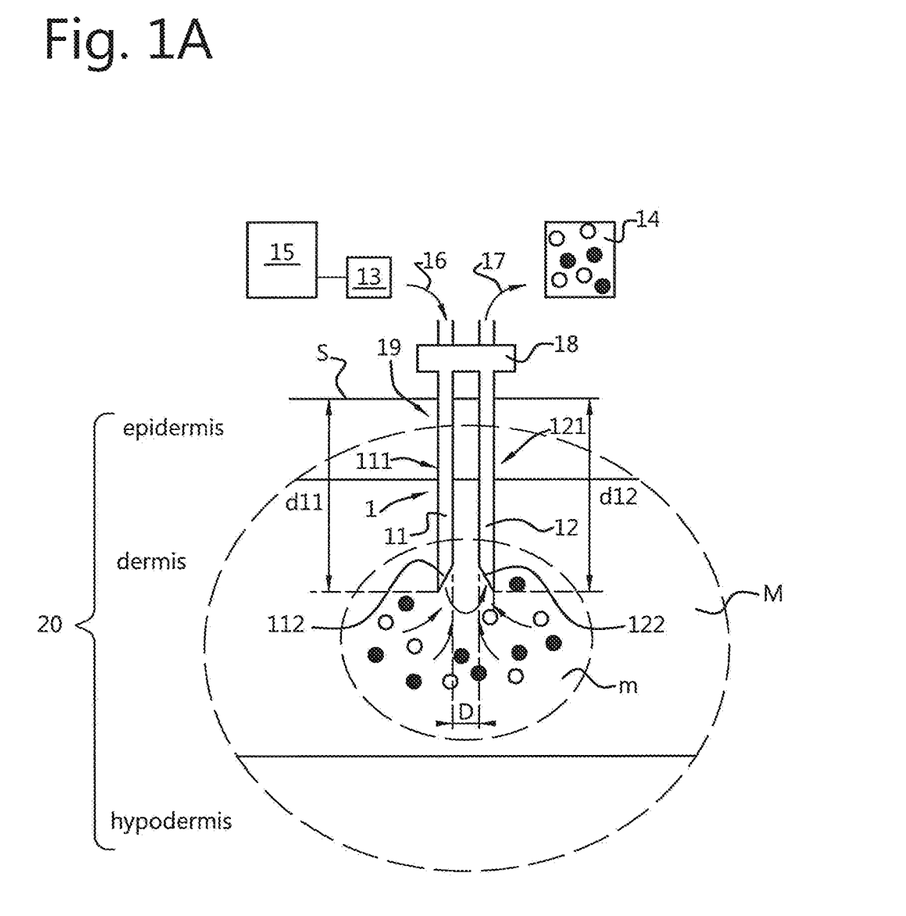
Figure 1B:
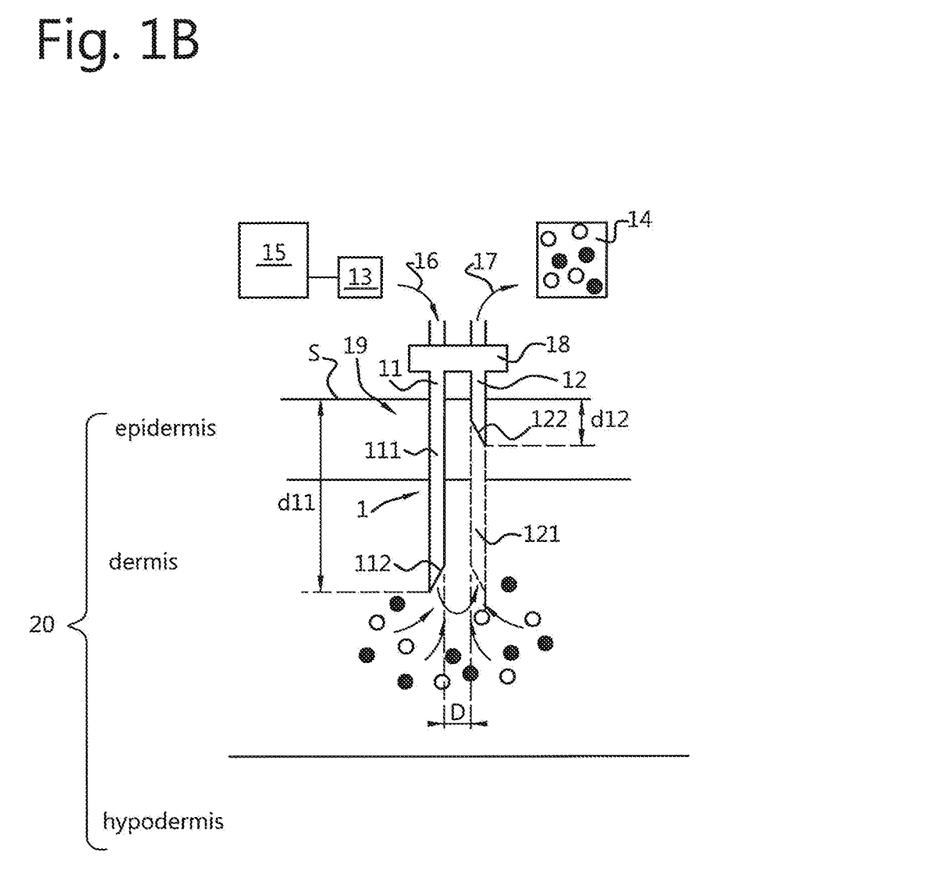
FIG. 1B schematically illustrates a second embodiment of an interstitial fluid removal device inserted in a tissue of a multicellular organism.
Figure 1C:
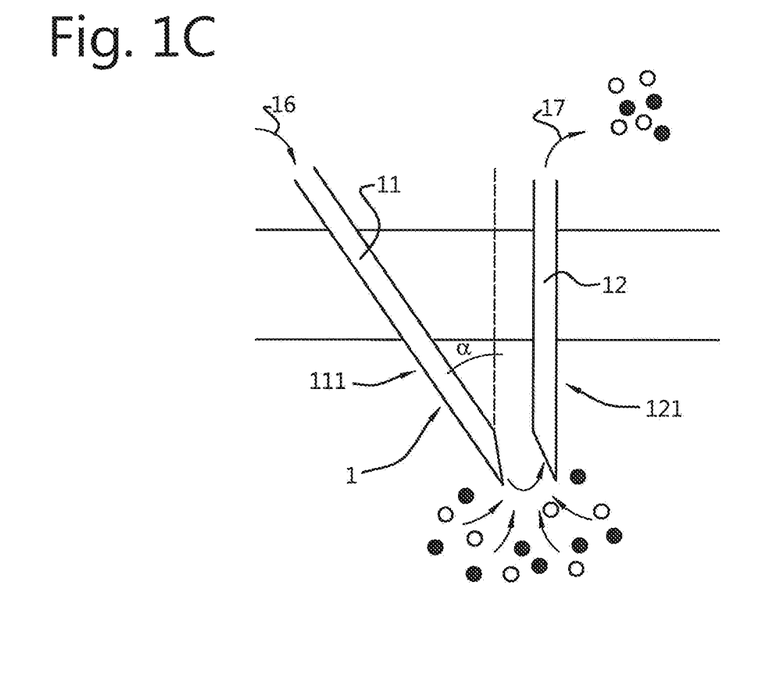

FIGS. 1A, 1B and 1C are here described simultaneously. All three figures show a first needle 11, here a microneedle, and a second needle 12, here a microneedle, of an interstitial fluid removal device 1. Both the first microneedle 11 and the second microneedle 12 are shown while they are inserted in a tissue 20. The first microneedle 11 defines a fluid inlet channel 111; the second microneedle 12 defines an interstitial fluid outlet channel 122.

With reference to FIG. 1B, it is shown that the second microneedle 12 may first be inserted in the tissue 20 as deep as the first microneedle 11, but afterwards partially retracted again. As the microneedle 12 has pierced the tissue 20, an interstitial fluid outlet channel 121 remains present. Typically said outlet channel 121, when piercing "alive" tissue, remains present for at least several hours.

It is noted that in the shown figures, the tissue of the multicellular organism is a skin tissue 20 of a human/a patient. It is to be understood that, alternatively, the tissue may of course be the skin of a non-human mammal, and/or an animal, and/or any other organism. Throughout the description of the figures, the wording "skin" will however be used.

The penetration depth d12 of the second microneedle 12, in use, is smaller than a penetration depth d11 of the first microneedle 11 in the embodiment of FIG. 1B. In such an embodiment, preferably the penetration depths d11, d12 are initially the same, and the second microneedle 12 is then (partially) retracted before operating the interstitial fluid removal device 1.

In the embodiment of FIG. 1B the second microneedle 12 remains inserted in the epidermis layer of the skin 20. It is possible that the second microneedle 12 is retracted more than illustrated here (e.g. completely removed from the skin 20) or retracted less than illustrated here (e.g. still in the dermis layer of the skin 20, but less deep than the first microneedle 11).

As shown in FIGS. 1A, 1B and 10, the second microneedle 12, and interstitial fluid outlet channel 121, are here arranged substantially perpendicular with respect to the skin surface S. The first microneedle 11 may also be arranged substantially perpendicular with respect to the skin surface S, as shown in FIGS. 1A and 1B, such that the first microneedle 11 and the second microneedle 12 are substantially parallel to each other. Alternatively the first microneedle 11 may be arranged at an angle α with respect to the second microneedle 12, as shown in FIG. 10. Angle α here has a magnitude of about 45°.

The skin 20 contains interstitial fluid (IF or ISF). When a tumor is present in said skin 20, e.g. when a patient suffers from skin cancer, the ISF contains altered (increased) levels of soluble signalling molecules and vesicles. These soluble signalling molecules and vesicles play a role in the promotion of tumor growth, impair the function of the local immune cells and/or prevent their infiltration in the tumor, as well as induce metastasis (the spreading of the tumor to other positions in the body) (Maman and Witz (2018), Nat. Rev. Cancer., Vol. 18(6), pages 359-376). By removing this ISF around a tumor or within a tumor, the tumor growth may be negatively affected.

Accordingly, the second needle 12 is arranged in fluid communication with a fluid extractor 14, which is configured for extracting interstitial fluid 17 from the skin 20.

It has however been found by the applicant that by initially removing ISF 17 with the microneedle 12, only small amounts of ISF 17 can be removed. Therefore, according to the invention a further microneedle 11 is provided. This first microneedle 11 is arranged in fluid communication with a fluid injector 13, which fluid injector 13 is arranged in fluid communication with a fluid source 15. For example, the fluid 16 in the fluid source 15 may contain at least partially one or more surface tension modifiers (e.g. polyethylene glycol derivatives), one or more osmolality modifiers (e.g. sodium chloride, sucrose, or water), one or more pH modifiers (e.g. bicarbonate buffers), one or more chelator agents (e.g. EDTA), and/or one or more bio-active molecules (e.g. proteins, drugs).

Through microneedle 11, fluid 16 can be inserted in skin 20. This fluid 16 will attract the soluble signalling molecules and vesicles in the micro-environment around the insertion location of the microneedle 11, said soluble signalling molecules and vesicles dissolving in the injected fluid 16, as schematically shown in FIGS. 1A, 1B and 10. When the fluid 16 contains such soluble signalling molecules and/or vesicles, it becomes interstitial fluid.

Tests have shown that it is physically impossible or very difficult to remove ISF 17 from the same location in the skin 20 for an elongated period of time, as after a while all interstitial fluid is drained from a micro-environment m surrounding the fluid outlet channel 121, the skin 20 collapses, and extraction of interstitial fluid 17 is no longer possible. However, by providing "fresh" carrier fluid 16 in the skin 20, this collapsing is prevented. The soluble signalling molecules and vesicles in the macro-environment M of the skin 20, surrounding the micro-environment m, will migrate from the interstitial fluid 17 in the macro-environment M towards the fluid 16 in the micro-environment m, dissolve therein, and are extracted through outlet channel 121, as shown. In this respect, preferably the openings of the needle tips 111, 112 face towards each other as can clearly be seen in FIGS. 1A, 1B and 10.

For example, the fluid injector 13 may be adapted to be operated with a flow rate of at least at least 6 µl/h.

For example, the fluid extractor 14 may be adapted to be operated with a flow rate of at least at least 6 µl/h.

For example, the fluid injector 13 and the fluid extractor 14 may be operated simultaneously and continuously for a few minutes, e.g. 5 minutes-10 minutes, 10 minutes-15 minutes, 15 minutes-30 minutes, and/or 30 minutes-60 minutes, or a few hours, e.g. 1 hour-2 hours, 1 hour-3 hours, 1 hour-5 hours, 5 hours or longer, e.g. 8 hours or longer, e.g. about 12 hours and/or about 24 hours or longer, such as about 48 hours or longer, to drain soluble signalling molecules and vesicles from skin 20.

Alternatively the fluid injector 13 and the fluid extractor 14 may be operated simultaneously and intermittently for a few minutes, e.g. 5 minutes-10 minutes, 10 minutes-15 minutes, 15 minutes-30 minutes, and/or 30 minutes-60 minutes, or a few hours, e.g. 1 hour-2 hours, 1 hour-3 hours, after which operation is stopped for a few minutes, e.g. 5 minutes-10 minutes, 10 minutes-15 minutes, 15 minutes-30 minutes, and/or 30 minutes-60 minutes, or a few hours, e.g. 1 hour-2 hours, 1 hour-3 hours, and the operation may be continued again for a few minutes, e.g. 5 minutes-10 minutes, 10 minutes-15 minutes, 15 minutes-30 minutes, and/or 30 minutes-60 minutes, or a few hours, e.g. 1 hour-2 hours, 1 hour-3 hours.

Yet alternatively, the fluid injector 13 may be operated first to inject fluid 16 in the skin 20 of a patient, e.g. for a few seconds such as 1-5 seconds or 1-10 seconds, operation may be stopped, e.g. for a few seconds or a few minutes, or longer, and then fluid extractor 14 is operated, e.g. for a few seconds. This process of separate and independent operation of the fluid injector 13 and fluid extractor 14 may then continue for several hours or even several days.

Also shown in FIGS. 1A and 1B is a housing 18 that fixes the microneedles 11, 12 at a predetermined distance D with respect to each other. Preferably said distance D is relatively small such that only low injection forces/pressures and low extraction forces/pressures are needed. For example the distance D may be smaller than 3 mm, preferably smaller than 2 mm, e.g. smaller than 1 mm, more preferably smaller than 0.5 mm, such as smaller than 0.1 mm, or smaller than 0.02 mm.

To allow a sufficiently large micro-environment m to be drained from the soluble signalling molecules and vesicles, the distance D between the first microneedle 11 and the second microneedle 12 may be larger than 0.01 mm, preferably larger than 0.015 mm, such as larger than 0.02 mm or about 0.02 mm.

As can be seen in the figures, the "distance" D between a needle tip 112 of the first needle 11 and a needle tip 122 of the second needle 12 is defined as the distance between the right wall portion of the left needle 11 and the left wall portion of the right needle 12 or, alternatively worded, the "minimal distance" between the needles, excluding the size (diameter) of the needles 11, 12 themselves.

It is noted that, although FIGS. 1A, 1B and 10 show an embodiment of the interstitial fluid removal device 1 wherein both needles 11, 12 are inserted in the skin 20 during operation of the device 1, an equivalent embodiment is conceivable wherein first an outflow channel is created by inserting a needle in a tissue of a multicellular organism, followed by the complete removal of the needle and the insertion of the needle in the skin again as "first" needle. A suction head or similar collector may then be provided on the skin at the location of the outflow channel and connected to the fluid extractor.

Figure 2:
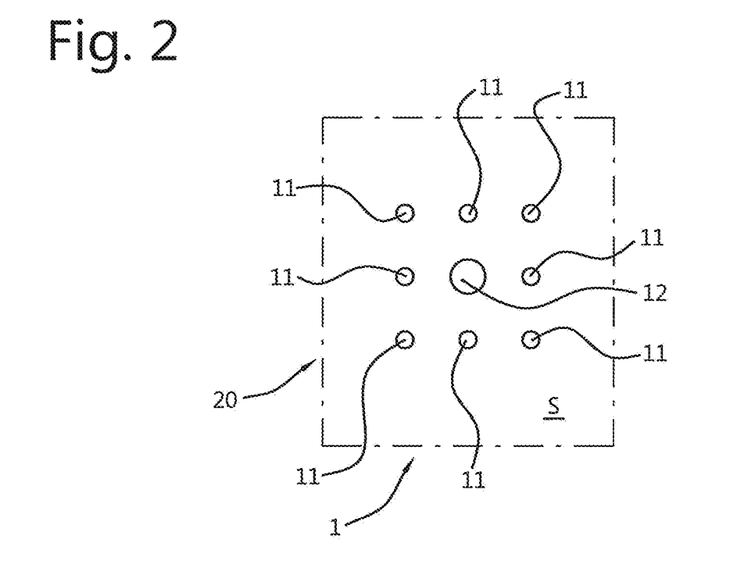
FIG. 2 schematically illustrates a top view of a tissue of a multicellular organism with inserted therein a fourth embodiment of an interstitial fluid removal device.

Turning to FIG. 2, a further embodiment of the interstitial fluid removal device 1 is shown wherein several first needles 11, here a total number of eight, are inserted in the skin 20 for injecting a fluid in said skin 20, and one second needle 12 is inserted in the skin 20 for extracting interstitial fluid from said skin 20. The second needle 12 is larger in diameter compared to the first needles 11. The arrangement of FIG. 2 may e.g. be used to allow the draining/flushing of a larger micro-environment of the skin 20, while needing less microneedles.

Although FIG. 2 shows an arrangement with more injection needles 11 than extraction needles 12, it is to be understood that, analogously, the interstitial fluid removal device 1 may comprise more extraction needles 12 than injection needles 11.

Figure 3:
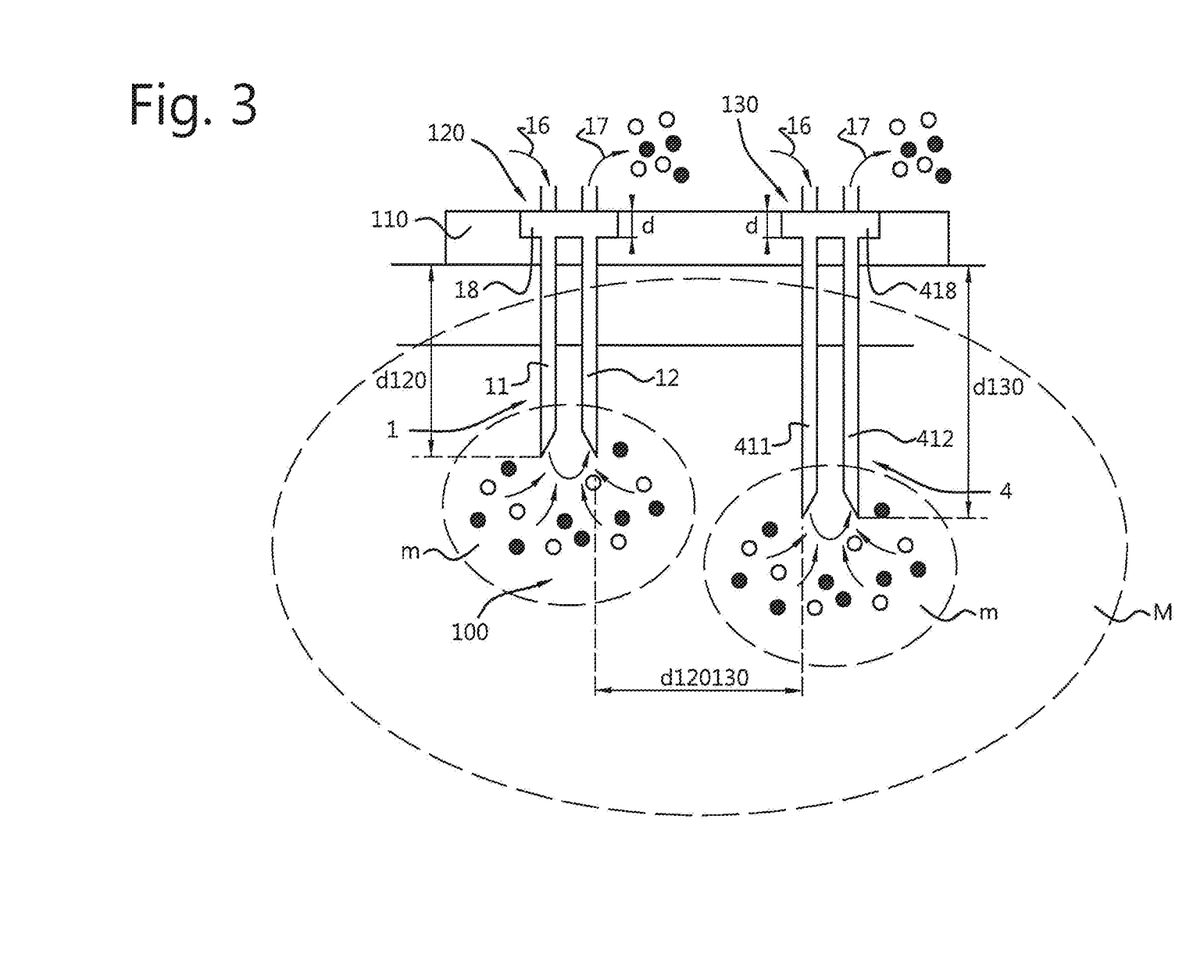
FIG. 3 schematically illustrates a first embodiment of an interstitial fluid removal system inserted in a tissue of a multicellular organism.

Turning to FIG. 3, an interstitial fluid removal system 100 is shown. The interstitial fluid removal system 100 comprises a patch member 110. The patch member 110 has at least two recesses 120, 130. In FIG. 3 only two recesses 120, 130 are shown, but it is well possible that the patch member 110 contains dozens or hundreds of recesses. The interstitial fluid removal system 100 further comprises at least two interstitial fluid removal devices 1, 4 as described in the above. Preferably the number of interstitial fluid removal devices 1, 4 is equal to the number of recesses, but this is not needed per se. Each of the interstitial fluid removal devices 1, 4 is arranged in a recess 120, 130 of the patch member 110.

As shown here, a distance d120130 between two interstitial fluid removal devices 1, 4 is larger than a distance D (see FIG. 1) between the two needles 11, 12 of the first interstitial fluid removal device 1 and also larger than a distance between the two needles 411, 412 of the second interstitial fluid removal device 4.

Like distance D, also distance d120130 is defined as the "minimum" distance between two needle pairs of two fluid removal devices 1, 4.

The penetration depth d120 of the first interstitial fluid removal device 1 may be different, here smaller, compared the penetration depth d130 of the second interstitial fluid removal device 4. This may be a result of an adaptation to the specific shape of the skin tumor to be treated. The difference in penetration depth may e.g. be accomplished by using needles of a different length (as shown here) and/or by changing the depth d of the recesses 120, 130 of the patch member 110.

Several or all of the first needles 11, 411 may be arranged in fluid communication with one fluid injector, the number of fluid injectors being smaller than the number of first needles, or each first needle 11, 411 may be arranged in fluid communication with its own fluid injector, the number of fluid injectors being equal to the number of first needles. Likewise, several or all of the second needles 12, 412 may be arranged in fluid communication with one fluid extractor, the number of fluid extractors being smaller than the number of second needles, or each second needle 12, 412 may be arranged in fluid communication with its own fluid extractor, the number of fluid extractors being equal to the number of second needles.

As shown here, the microenvironments m do not overlap and are separate from each other. Alternatively, but not shown, the microenvironments m may touch and/or overlap.

Figure 5:
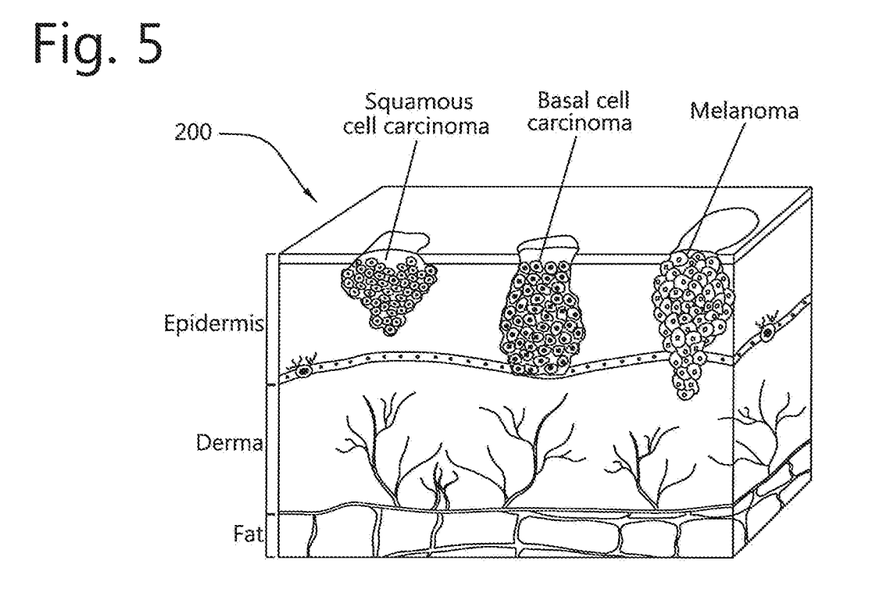
FIG. 5 schematically illustrates a 3D representation of a skin tumor.

With respect to FIG. 5, wherein a representation of a skin tumor 200 is shown and FIG. 3, wherein an interstitial fluid removal system 100 is shown, a further aspect of the invention relates to a method for manufacturing an interstitial fluid removal system 100, comprising the steps of:
- providing a 3D clinical representation of a skin tumor of a patient;
- designing a patch member 110 based on said clinical representation, the patch member 110 having at least two recesses 120, 130, at least two of the recesses 120, 130 preferably having a different depth d;
- placing a housing 18 in at least two of the recesses 120, 130, the housing 18 comprising at least a first needle 11 and a second needle 12;
- fluidly coupling the first needles 11 of the housings 18 to one or more fluid injectors;
- fluidly coupling the second needles 12 of the housings 18 to one or more interstitial fluid extractors.

A further aspect of the invention relates to a method for treating a subject with skin tumor, the method comprising the step of removing an amount of interstitial fluid 17 from said skin tumor with the interstitial fluid removal device 1 according to the above or an interstitial fluid removal system 100 according to the above.

Figure 4A:
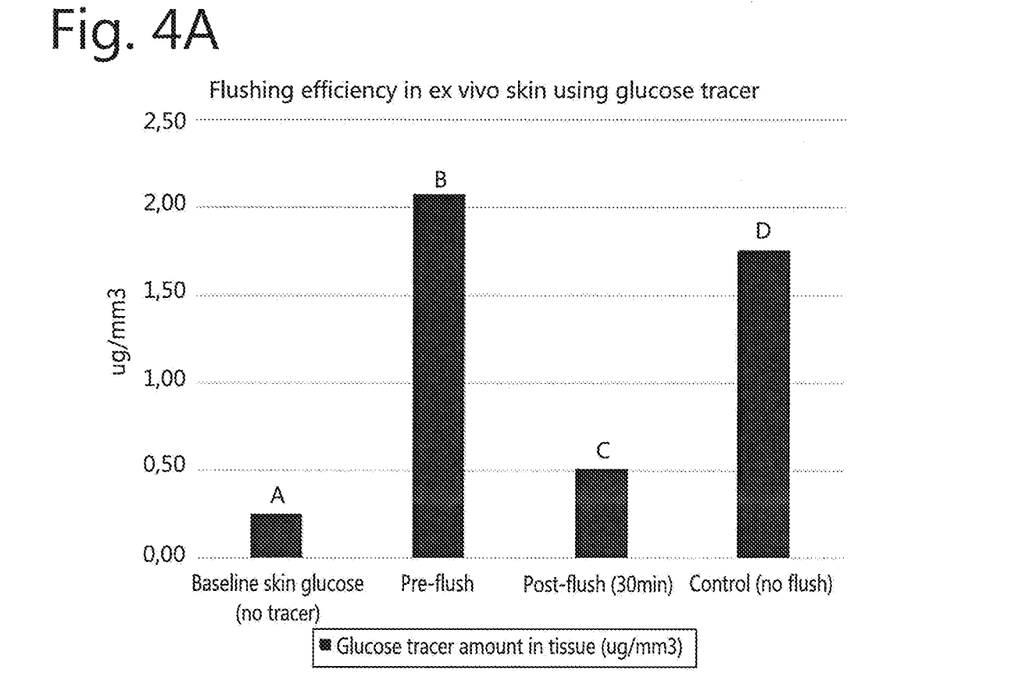
FIGS. 4A and 4B schematically illustrate preliminary test results obtained with embodiments of the interstitial fluid removal device.

With reference to FIGS. 4A and 4B, some preliminary test results obtained with the interstitial fluid removal device 1 according to the embodiments shown herein are explained. With reference to FIG. 4A, bar A represents the natural level of glucose in a test skin. Bar B represents the level of glucose in the same test skin just after an amount of glucose is injected therein. The same amount of glucose is injected in two different skins, which different skins have the same natural level of glucose. In a first of the two skins, no treatment is performed after injection of glucose, and the natural dissipation of glucose is measured. The result after a waiting time of 30 minutes is shown in bar D. In a second of the two skins treatment (flushing) with the interstitial fluid removal device is performed for a total duration of 30 minutes, wherein the fluid injector and the fluid extractor were operated simultaneously. The result of this treatment is shown in bar C. As can be derived from the difference between bar D and bar C, the interstitial fluid removal device is able to remove a significant amount of glucose from the skin within 30 minutes, reducing the glucose concentration from more than 8 times the natural level to less than 2 times the natural level in 30 minutes, whereas the natural dissipation only reduces the glucose concentration to about 7 times the natural level in the same amount of time.

Figure 4B:
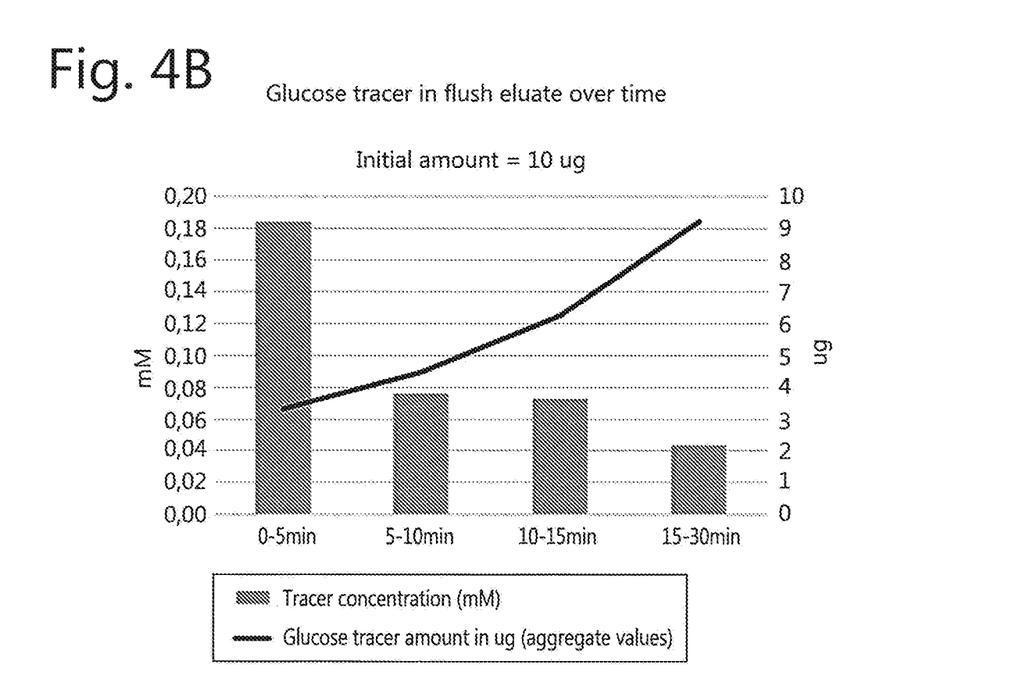

With reference to FIG. 4B, the average concentration of glucose in the extracted interstitial fluid of the second skin is shown. As expected, initially this concentration is relatively high (as there is more glucose in the skin), and the concentration gradually drops when the interstitial fluid removal device is operated for a longer period of time. Importantly, also after operation for more than 15 minutes glucose is still removed from the skin when operating the interstitial fluid removal device.

Figure 6:
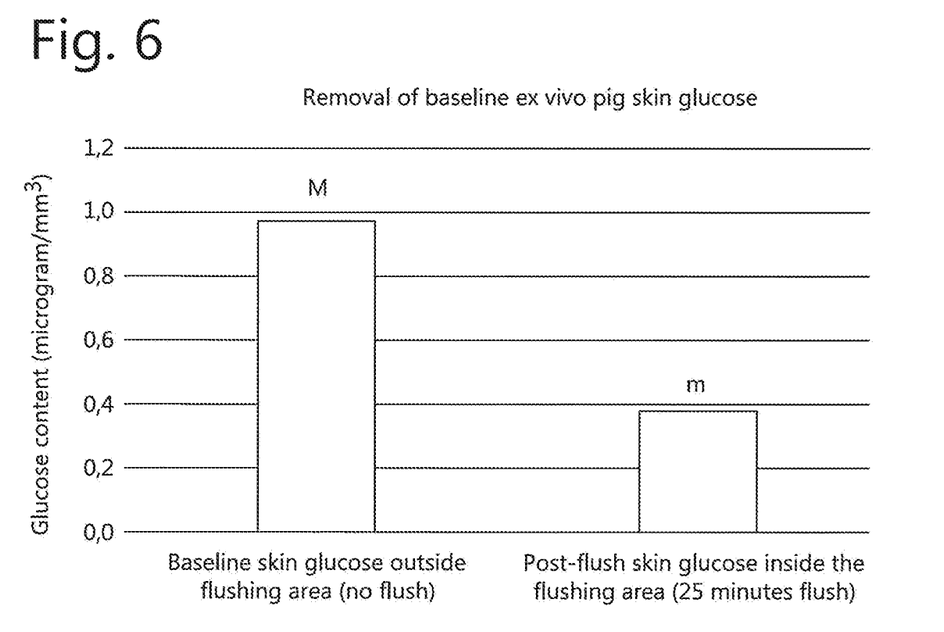
FIG. 6 schematically illustrates further preliminary test results obtained with embodiments of the interstitial fluid removal device.

FIG. 6 shows the result of another experiment carried out with the interstitial fluid removal device as shown herein. A fresh pig skin (obtained immediately after euthanasia and cooled at 4° C. during transport to the laboratory as well as during preparation) was defatted until it reached a thickness of 3 mm, keeping the epidermis layer and the dermis layer of the skin intact, as well as a small portion of the underlying fat tissue. Glucose was injected in the skin.

A first needle, having a diameter of 230 µm, was inserted in the skin at a depth of 1 mm to provide a fluid inlet channel. The first needle was connected to a fluid injector, here a micro-peristaltic pump, to allow the injection of a carrier fluid, here phosphate buffered saline (PBS), in the skin.

A second needle, also having a diameter of 230 µm, was inserted in the skin at a depth of 1 mm to provide an interstitial fluid outlet channel. The second needle was connected to a fluid extractor, here a micro-peristaltic pump, to allow interstitial fluid to be extracted from the skin.

The first needle and the second needle were fixed in a housing at a distance of 350 µm from each other.

The first and the second needle were consecutively operated simultaneously, at an injection rate of 30 µL/min and an extraction rate of 30 µL/min for a duration of 25 minutes, to allow glucose from the microenvironment surrounding the first and second needle to mix with the injected PBS and to be extracted with the second needle.

After the 25 minutes an amount of interstitial fluid was obtained from the microenvironment surrounding the first and second needle, and an amount of interstitial fluid was obtained from the macro-environment surrounding the microenvironment. The interstitial fluid from both samples was tested and the results are indicated in FIG. 6. As can be shown, the amount of glucose in the macro-environment (bar M) is larger than in the micro-environment (bar m). This shows that the interstitial fluid removal device is effective in removing glucose from a skin.

Figure 7:
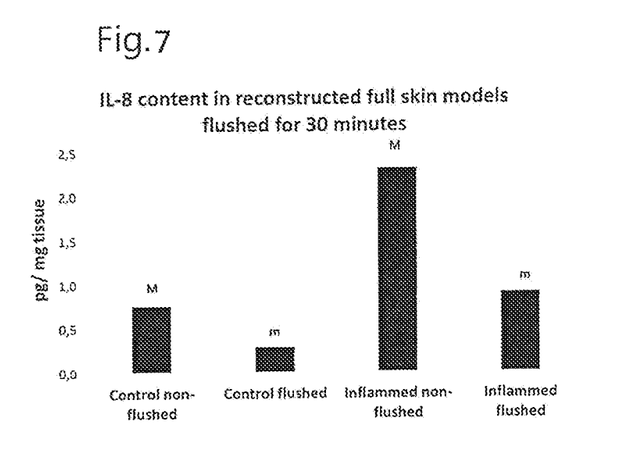
FIG. 7 schematically illustrates yet further preliminary test results obtained with embodiments of the interstitial fluid removal device.

With reference to the test data of FIG. 7, in a similar test also the removal of proteins from the interstitial fluid of a test skin has been shown. In this case the test skin was a reconstructed human skin. In this case, the protein was IL-8. As shown in the comparative figure, IL-8 can successfully be removed from the interstitial fluid of a reconstructed human skin with the interstitial fluid removal device as presented herein.

These and other embodiments of the present invention are defined in the clauses below:

1. Interstitial fluid removal device comprising a first needle, a second needle, a fluid injector and an interstitial fluid extractor,
   the first needle being configured for insertion in a tissue of a multicellular organism to provide a fluid inlet channel;

the second needle being configured for insertion in a tissue of a multicellular organism to provide an interstitial fluid outlet channel;

the fluid injector being arranged in fluid communication with both a fluid source and the first needle and configured to inject a fluid in the tissue of the multicellular organism;

the fluid extractor being arranged in fluid communication with the second needle and configured to extract interstitial fluid from the tissue of the multicellular organism, wherein the fluid injector and the fluid extractor are independently and/or simultaneously operable with respect to each other.

2. Interstitial fluid removal device according to clause 1, wherein a penetration depth of the first needle is larger than a penetration depth of the second needle.

3. Interstitial fluid removal device according to any one of the preceding clauses, wherein the second needle is configured for insertion in the tissue of a multicellular organism substantially perpendicular with respect to a surface defined by said tissue.

4. Interstitial fluid removal device according to any one of the preceding clauses, wherein the first needle is configured for insertion in the tissue of a multicellular organism at an angle of between 20° and 70° with respect to the second needle.

5. Interstitial fluid removal device according to any one of the preceding clauses, wherein the second needle is configured to be at least partially extracted from said tissue after insertion therein and before the fluid extractor is operated.

6. Interstitial fluid removal device according to any one of the preceding clauses, wherein a distance between a needle tip of the first needle and a needle tip of the second needle is smaller than 3 mm, preferably smaller than 2 mm, e.g. smaller than 1 mm, more preferably smaller than 0.5 mm, such as smaller than 0.1 mm or about 0.02 mm or smaller.

7. Interstitial fluid removal device according to any one of the preceding clauses, wherein a distance between a needle tip of the first needle and a needle tip of the second needle is larger than 0.01 mm, preferably larger than 0.015 mm, such as larger than 0.02 mm.

8. Interstitial fluid removal device according to any one of the preceding clauses, wherein the first needle and the second needle are configured for insertion in a skin of an animal, e.g. a mammal, more particularly a human, preferably in the dermis layer of said skin.

9. Interstitial fluid removal device according to any one of the preceding clauses, further comprising a housing for receiving a needle pair, said first needle and said second needle forming said needle pair.

10. Interstitial fluid removal device according to any one of the preceding clauses, wherein the fluid is a fluid selected from the list comprising surface tension modifiers, osmolality modifiers, pH modifiers, chelating agents, and bio-active molecules.

11. Interstitial fluid removal device according to any one of the preceding clauses, wherein the fluid injector has a flow rate of at least 6 µl/h.

12. Interstitial fluid removal system, comprising a patch member which includes at least two recesses and at least two interstitial fluid removal devices according to any one of the clauses 1-11, a said interstitial fluid removal device being arranged in at least two of said recesses.

13. Interstitial fluid removal system according to clause, wherein a penetration depth of the interstitial fluid removal device arranged in a first one of said recesses differs from a penetration depth of the interstitial fluid removal device arranged in a second one of said recesses.

14. Method for manufacturing an interstitial fluid removal system, comprising the steps of:

providing a 3D clinical representation of a skin tumor of a patient;

designing a patch member based on said clinical representation, the patch member having at least two recesses, at least two of the recesses preferably having a different depth;

placing a housing in at least two of the recesses, the housing comprising at least a first needle and a second needle;

fluidly coupling the first needles of the housings to one or more fluid injectors;

fluidly coupling the second needles of the housings to one or more interstitial fluid extractors.

15. A method for treating a subject with skin tumor, the method comprising the step of removing an amount of interstitial fluid from said skin tumor with the interstitial fluid removal device according to any of the clauses 1-11 or an interstitial fluid removal system according to clause 12 or 13.

LIST OF REFERENCE NUMERALS

1 Interstitial fluid removal device
11 first needle
111 fluid inlet channel
112 first needle tip
12 second needle
121 interstitial fluid outlet channel
122 second needle tip
13 fluid injector
14 interstitial fluid extractor
15 fluid source
16 fluid
17 interstitial fluid
18 housing
19 needle pair
4 Interstitial fluid removal device
411 first needle
412 second needle
418 housing
20 skin
100 interstitial fluid removal system
110 patch member
120 recess
130 recess
200 representation of a skin tumor
d recess depth
D distance between first needle tip and second needle tip
d11 penetration depth first needle
d12 penetration depth second needle
d120 penetration depth first interstitial fluid removal device
d130 penetration depth second interstitial fluid removal device
m micro-environment
M macro-environment
S skin surface
α angle between first needle and second needle

The invention claimed is:

1. An interstitial fluid removal device comprising a first needle, a second needle, a fluid injector and an interstitial fluid extractor, the first needle being configured for insertion in a tissue of a multicellular organism to provide a fluid inlet channel;

the second needle being configured for insertion in a tissue of a multicellular organism to provide an interstitial fluid outlet channel;

the fluid injector being arranged in fluid communication with both a fluid source and the first needle and configured to inject a fluid in the tissue of the multicellular organism;

the interstitial fluid extractor being arranged in fluid communication with the second needle and configured to extract interstitial fluid from the tissue of the multicellular organism, wherein the fluid injector and the interstitial fluid extractor are independently operable with respect to each other, wherein a distance between a needle tip of the first needle and a needle tip of the second needle is smaller than 3 mm, and wherein an opening of the needle tip of the first needle and an opening of the needle tip of the second needle face towards each other.

2. The interstitial fluid removal device according to claim 1, wherein a penetration depth of the first needle is larger than a penetration depth of the second needle.

3. The interstitial fluid removal device according to claim 1, wherein the second needle is configured for insertion in the tissue of the multicellular organism perpendicular with respect to a surface defined by said tissue.

4. The interstitial fluid removal device according to claim 1, wherein the first needle is configured for insertion in the tissue of the multicellular organism at an angle of between 20° and 70° with respect to the second needle.

5. The interstitial fluid removal device according to claim 1, wherein the second needle is configured to be at least partially extracted from said tissue after insertion therein and before the fluid extractor is operated.

6. The interstitial fluid removal device according to claim 1, wherein said distance between the needle tip of the first needle and the needle tip of the second needle is smaller than 2 mm.

7. The interstitial fluid removal device according to claim 1, wherein the distance between the needle tip of the first needle and the needle tip of the second needle is larger than 0.01 mm.

8. The interstitial fluid removal device according to claim 1, wherein the first needle and the second needle are configured for insertion in a skin of an animal.

9. The interstitial fluid removal device according to claim 1, further comprising a housing for receiving a needle pair, wherein said first needle and said second needle forms said needle pair.

10. The interstitial fluid removal device according to claim 1, wherein the fluid is selected from the group consisting of surface tension modifiers, osmolality modifiers, pH modifiers, chelating agents, and bio-active molecules.

11. The interstitial fluid removal device according to claim 1, wherein the fluid injector has a flow rate of at least 6 µl/h.

12. A method for treating a subject with skin tumor, the method comprising a step of removing an amount of the interstitial fluid from said skin tumor with the interstitial fluid removal device according to claim 1.

13. An interstitial fluid removal system, comprising a patch member which includes at least two recesses and at least two interstitial fluid removal devices according to claim 1, a first one of said at least two interstitial fluid removal devices being arranged in a first recess of said at least two recesses.

14. The interstitial fluid removal system according to claim 13, wherein a penetration depth of the first one of the at least two interstitial fluid removal devices arranged in the first recess of said at least two recesses differs from a penetration depth of a second one of the interstitial fluid removal devices arranged in a second recess of said at least two recesses.

15. A method for treating a subject with skin tumor, the method comprising a step of removing an amount of the interstitial fluid from said skin tumor with the interstitial fluid removal system according to claim 12.

16. A method for manufacturing the interstitial fluid removal system according to claim 13, comprising the steps of:

providing a 3D clinical representation of a skin tumor of a patient;

designing the patch member based on said clinical representation, the patch member having the at least two recesses;

providing at least two housings;

placing a first one of the at least two housings in the first recess of the at least two recesses, the first one of the at least two housings comprising the first needle and the second needle, wherein at least lengths of the first needle and the second needle are based on said clinical representation;

fluidly coupling the first needle of the first one of the at least two housings to one or more fluid injectors; and fluidly coupling the second needle of the first one of the at least two housings to one or more interstitial fluid extractors.

17. The method according to claim 16, wherein the two recesses of the at least two recesses have a different depth.

18. An interstitial fluid removal device comprising a first needle, a second needle, a fluid injector and an interstitial fluid extractor, the first needle being configured for insertion in a tissue of a multicellular organism to provide a fluid inlet channel;

the second needle being configured for insertion in a tissue of a multicellular organism to provide an interstitial fluid outlet channel;

the fluid injector being arranged in fluid communication with both a fluid source and the first needle and configured to inject a fluid in the tissue of the multicellular organism; and the interstitial fluid extractor being arranged in fluid communication with the second needle and configured to extract interstitial fluid from the tissue of the multicellular organism, wherein the fluid injector and the interstitial fluid extractor are simultaneously operable, wherein a distance between a needle tip of the first needle and a needle tip of the second needle is smaller than 3 mm, and wherein an opening of the needle tip of the first needle and an opening of the needle tip of the second needle face towards each other.

19. An interstitial fluid removal system, comprising a patch member, which includes at least two recesses and at least two interstitial fluid removal devices according to claim 18, a first one of said at least two interstitial fluid removal devices being arranged in a first recess of said at least two recesses.

20. A method for treating a subject with skin tumor, the method comprising a step of removing an amount of the interstitial fluid from said skin tumor with the interstitial fluid removal device according to claim 18.

* * * * *